(12) United States Patent
Huang et al.

(10) Patent No.: US 11,434,200 B2
(45) Date of Patent: Sep. 6, 2022

(54) SOLID FORMS COMPRISING AN OXIME ETHER COMPOUND AND A COFORMER, COMPOSITIONS AND METHODS OF USE THEREOF

(71) Applicant: Novartis AG, Basel (CH)

(72) Inventors: Lianfeng Huang, Basking Ridge, NJ (US); Daozhong Zou, Raritan, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/905,441

(22) Filed: Jun. 18, 2020

(65) Prior Publication Data

US 2021/0139420 A1 May 13, 2021

Related U.S. Application Data

(63) Continuation of application No. 15/915,931, filed on Mar. 8, 2018, now abandoned.

(60) Provisional application No. 62/469,146, filed on Mar. 9, 2017.

(51) Int. Cl.
| | | |
|---|---|---|
| *C07D 205/04* | (2006.01) | |
| *A61K 47/22* | (2006.01) | |
| *A61K 9/48* | (2006.01) | |
| *A61K 9/20* | (2006.01) | |
| *A61K 47/10* | (2017.01) | |

(52) U.S. Cl.
CPC .............. *C07D 205/04* (2013.01); *A61K 9/20* (2013.01); *A61K 9/48* (2013.01); *A61K 47/10* (2013.01); *A61K 47/22* (2013.01); *C07B 2200/13* (2013.01)

(58) Field of Classification Search
CPC .................................................... C07D 205/04
See application file for complete search history.

(56) References Cited

FOREIGN PATENT DOCUMENTS

WO    WO2010/002586    *    1/2010

OTHER PUBLICATIONS

Y. Mao-Draayer et al., Clinical Immunology 175 (2017) 10-15.*
Pan et al., ACS Med. Chem. Lett. 2013, 4, 333-337.*
Shah et al., Journal of Pharmaceutical Sciences, vol. 95, No. 8, Aug. 2006, 1641-1665.*
Shindler et al. J. Neurophthalmol. Dec. 2010; 30(4): 328-339.*

* cited by examiner

*Primary Examiner* — Rebecca L Anderson
(74) *Attorney, Agent, or Firm* — Finnegan, Henderson, Farabow, Garrett & Dunner, LLP (57) ABSTRACT

Provided herein are formulations, processes, solid forms and methods of use relating to (E)-1-(4-(1-(((4-cyclohexyl-3-(trifluoromethyl)benzyl)oxy)imino)ethyl)-2-ethylbenzyl)azetidine-3-carboxylic acid.

24 Claims, 4 Drawing Sheets

SOLID FORMS COMPRISING AN OXIME ETHER COMPOUND AND A COFORMER, COMPOSITIONS AND METHODS OF USE THEREOF

This application is a continuation of U.S. application Ser. No. 15/915,931, filed on Mar. 8, 2018, which claims the benefit of U.S. Provisional Application No. 62/469,146, filed on Mar. 9, 2017, which are incorporated herein by reference in their entirety.

1. FIELD

Provided herein are solid forms comprising (E)-1-(4-(1-(((4-cyclohexyl-3-(trifluoromethyl)benzyl)oxy)imino) ethyl)-2-ethylbenzyl)azetidine-3-carboxylic acid and a coformer. Pharmaceutical compositions comprising such solid forms (e.g., cocrystals) and methods of use of such solid forms for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune or chronic inflammatory diseases include Graves' disease, Type 1 diabetes, multiple sclerosis, inflammatory bowel disease, systemic lupus, polymyositis, dermatomyositis, lupus nephritis, rheumatoid arthritis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. In recent years, pharmaceutical cocrystals have emerged as a possible alternative approach to modulate or enhance the physical and chemical properties of drug products. Cocrystals are crystalline solids composed of two or more different compounds bound together in a crystal lattice. Pharmaceutical cocrystals are cocrystals of a therapeutic compound, e.g., an active pharmaceutical ingredient ("API"), and one or more non-volatile compound(s) (referred to herein as coformer). A coformer in a pharmaceutical cocrystal is typically a non-toxic pharmaceutically acceptable molecule.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31: 875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56: 301-319 ("Price"); and Bernstein, 2004, "Crystal Structure Prediction and Polymorphism," *ACA Transactions* 39: 14-23 (a great deal still needs to be learned and done before one can state with any degree of confidence the ability to predict a crystal structure, much less polymorphic forms)).

3. SUMMARY

Provided herein are solid forms (e.g., cocrystal forms or mixtures thereof) comprising Compound 1:

having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof, and a coformer. Also provided herein are methods of preparing, isolating, and characterizing the solid forms.

Also provided herein are pharmaceutical compositions and single unit dosage forms, which comprise one or more solid forms provided herein.

A solid form is provided herein comprises (a) Compound 1; and (b) a coformer. In certain embodiments, the conformer is resveratrol, caffeine, theophyline, isonicotinamide, urea, nicotinamide, L-prolinamide, ascorbic acid, vanillin, methyl paraben, xylitol, sodium chloride, glycine, adenine, 2-aminopyridine, acetamide, saccharin, propyl paraben, vanillyl alcohol, chrysin, gentisic acid, lysine, glutamine, or menthol. In a particular embodiment, the conformer is resveratrol.

In certain embodiments, the solid form is substantially crystalline. In certain embodiments, the solid form can substantially be a cocrystal. In certain embodiments, the solid form is greater than 80% by weight, greater than 90% by weight, greater than 95% by weight, greater than 97% by weight, or greater than 99% by weight of a cocrystal. In certain embodiments, the solid form is substantially physically pure. In certain embodiments, the solid form is substantially free of other solid forms of Compound 1. In certain embodiments, the solid form further comprises amorphous Compound 1.

In certain embodiments, one crystal form provided herein has an X-ray powder diffraction pattern comprising one or more characteristic X-ray powder diffraction peaks at a two-theta angle of approximately 2.4, 5.1, 8.9, 1.3, 12.9, 14.2, 15.1, 17.5, 18.3, 19.3, 20.1, 20.7, 22.5, 25.7, 27.1, and 28.4 degrees. In certain embodiments, one crystal form provided herein has an X-ray powder diffraction pattern comprising one or more characteristic X-ray powder diffraction peaks at a two-theta angle of approximately 2.4, 5.1, 14.2, 15.1, 17.5, 18.3, 19.3, 20.1, 20.7, 22.5, 27.1, and 28.4 degrees. In certain embodiments, one crystal form provided herein has an X-ray powder diffraction pattern comprising one or more characteristic X-ray powder diffraction peaks at a two-theta angle of approximately 2.4, 5.1, 15.1, 17.5, 20.1, and 22.5 degrees. In certain embodiments, the crystal form can be solvated by diisopropyl ether (IPE), isopropyl alcohol (IPA), methyl isobutyl ketone (MIBK), acetonitrile (MeCN), nitromethane, t-butyl methyl ether (MTBE), ethyl acetate or heptanes. In a particular embodiment, the crystal form is solvated by diisopropyl ether.

Also provided are pharmaceutical compositions comprising the solid forms provided herein. In certain embodiments, the pharmaceutical compositions can further comprise a pharmaceutically acceptable excipient or carrier. In certain embodiments, the pharmaceutical compositions can be a single unit dosage form. In certain embodiments, the pharmaceutical compositions can be a tablet or a capsule.

In certain embodiments, the solid forms and the pharmaceutical compositions provided herein can be used as a medicament. In certain embodiments, solid forms of Compound 1 are useful for treating a subject suffering from or at risk for having an autoimmune disease or chronic inflammatory disorder. In certain embodiments, the solid form and the pharmaceutical composition can be used in methods for polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis. In a preferred embodiment, the multiple sclerosis is relapsing-remitting multiple sclerosis, primary progressive multiple sclerosis, secondary progressive multiple sclerosis, or relapsing secondary progressive multiple sclerosis. In certain embodiments, the methods comprise administering an effective amount of a solid form or a pharmaceutical composition to a subject in need thereof.

The present embodiments can be understood more fully by reference to the detailed description and examples, which are intended to exemplify non-limiting embodiments.

5. DETAILED DESCRIPTION

5.1 Definitions

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffractometry (PXRD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), PXRD, single-crystal X-ray diffractometry, vibrational spectroscopy, e.g., IR and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 0.5%, 1%, 0.5%, or 0.25% of the recited value or range of values. For example, in some embodiments, the value of an PXRD peak position may vary by up to ±0.2 degrees two theta while still describing the particular PXRD peak.

As used herein, and unless otherwise specified, a crystalline that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein and unless otherwise indicated, the term "substantially pure" when used to describe a solid form of a compound, i.e., a crystal form or an amorphous form of a compound, means a crystal form or an amorphous form of the compound that comprises that crystal form or amorphous form and is substantially free of other solid forms of the compound. A substantially pure crystal form is no less than about 95% pure, no less than about 96% pure, no less than about 97% pure, no less than about 98% pure, no less than about 98.5% pure, no less than about 99% pure, no less than about 99.5% pure, or no less than about 99.8% pure. In certain embodiments, a form that is substantially pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other polymorphs on a weight basis.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2%, 0.1%, 0.05%, or 0.01% by weight of the other compound, solid form, or composition.

As used herein, and unless otherwise indicated, the terms "solvate" and "solvated" refer to a solid form of a substance which contains solvent. The terms "solvate" and "solvated," as used herein, can also refer to a solvate of a salt, cocrystal, or molecular complex.

As used herein, and unless otherwise indicated, the terms "hydrate" and "hydrated" refer to a solvate wherein the solvent is water. The terms "hydrate" and "hydrated," as used herein, can also refer to a hydrate of a salt, cocrystal, or molecular complex.

As used herein, and unless otherwise indicated, the term "desolvated solvate," refers to a solid form of a substance which can be made by removing the solvent from a solvate.

As used herein, and unless otherwise indicated, the term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

As readily understood by one skilled in the art, a wide variety of functional groups and other structures may exhibit tautomerism and all tautomers of Compound 1 are within the scope of the present invention.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," as used herein, it is meant a diluent, excipient, or carrier in a formulation must be compatible with the other ingredient(s) of the formulation and not deleterious to the recipient thereof.

As used herein, and unless otherwise indicated, the term "solid form" refers to a physical form which is not predominantly in a liquid or a gaseous state. The term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form 1.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23$^{rd}$ ed., 1843-1844 (1995).

As used herein, and unless otherwise indicated, the term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

As used herein, and unless otherwise indicated, the term "cocrystal" refers to a crystalline material comprised of Compound 1, including tautomers thereof, and one or more non-volatile compounds bound together in a crystal lattice by non-covalent interactions. As used herein, and unless otherwise indicated, the term "coformer" refers to the one or more non-volatile compounds bound with Compound 1.

As used herein, and unless otherwise indicated, the term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject or patient is a non-human animal, in another embodiment a non-human mammal. In another embodiment, a subject or patient is a human having or at risk for having an autoimmune or chronic inflammatory disease. In certain embodiments, the autoimmune or chronic inflammatory disease is polymyositis, dermatomyositis, lupus nephritis, rheumatoid arthritis, inflammatory bowel disease, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease or multiple sclerosis. In certain embodiments, provided herein are methods for treating a subject suffering from or at risk for having relapsing-remitting multiple sclerosis, primary progressive multiple sclerosis, secondary progressive multiple sclerosis, and relapsing secondary progressive multiple sclerosis. In certain embodiments, a subject or patient is a human having or at risk for having a neurological disorder. In certain embodiments, the neurological disorder is Rett Syndrome. In certain embodiments, a subject or patient is a human having or at risk for having renal or hepatic impairment. In certain embodiments, a subject or patient is a human having or at risk for having a disease or disorder associated with sphingosine 1-phosphate, including but not limited to multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, and Graves' disease.

In certain embodiments, a subject or patient is a human having or at risk for having a disease or disorder associated with the interferon alpha receptor 1, including but not limited to psoriasis, ulcerative colitis, systemic lupus, multiple sclerosis, and rheumatoid arthritis. In certain embodiments, a subject or patient is a human having a disease or disorder mediated by lymphocyte interactions, such as, for example, in transplantation, such as acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus.

As used herein, and unless otherwise indicated, the term "zwitterion(s)" means compound(s) containing both a basic moiety, including but not limited to, for example, pyridine and imidazole; and an acidic moiety including but not limited to, for example, a carboxylic acid.

Unless otherwise specified, to the extent that there is a discrepancy between a depicted chemical structure of a compound provided herein and a chemical name of a compound provided herein, the chemical structure shall control.

5.2 Compound 1

The solid forms, formulations, and methods of use provided herein relate to solid forms (e.g., cocrystals) of Compound 1:

I having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof. Compound 1 can be prepared by methods known in the art. See, e.g., International Patent Application Publication No. WO 2013/113915 A1.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Form Cocrystals of Compound 1

While not intending to be bound by any particular theory, certain solid form cocrystals are characterized by physical properties, e.g., stability, solubility and dissolution rate, appropriate for pharmaceutical and therapeutic dosage forms. Moreover, while not wishing to be bound by any particular theory, certain solid form cocrystals are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid form cocrystals suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

In one embodiment, provided herein are solid forms (e.g., crystal forms, amorphous forms, or mixtures thereof) comprising (a) Compound 1; and (b) a coformer. In one embodiment, provided herein are solid forms (e.g., crystal forms, amorphous forms, or mixtures thereof) comprising (a) a free base of Compound 1; and (b) a coformer. In certain embodiments, the solid form comprises (a) a free acid of Compound 1; and (b) a coformer. In certain embodiments, the solid form comprises (a) a zwitterion of Compound 1; and (b) a coformer. Compound 1 can be synthesized or obtained according to a method known in the literature or based upon the teachings herein, including the methods described in detail in the examples herein.

In certain embodiments, the coformer is resveratrol, caffeine, theophyline, isonicotinamide, urea, nicotinamide, L-prolinamide, ascorbic acid, vanillin, methyl paraben, xylitol, sodium chloride, glycine, adenine, 2-aminopyridine, acetamide, saccharin, propyl paraben, vanillyl alcohol, chrysin, gentisic acid, lysine, glutamine, or menthol. In a particular embodiment, the coformer is resveratrol.

In one embodiment, solid forms provided herein may be a crystal form or an amorphous form or mixtures thereof (e.g., mixtures of crystal forms, or mixtures of crystal and amorphous forms), which comprises (a) Compound 1; and (b) a coformer. In one embodiment, provided herein is a crystal form comprising (a) Compound 1; and (b) a coformer. In one embodiment, provided herein is a cocrystal comprising (a) Compound 1; and (b) a coformer. In one embodiment, provided herein is an amorphous form comprising (a) Compound 1; and (b) a coformer. In one embodiment, provided herein is a mixture comprising (i) a cocrystal comprising (a) Compound 1; and (b) a coformer; and (ii) a crystal form of Compound 1. In one embodiment, provided herein is a mixture comprising (i) a cocrystal comprising (a) Compound 1; and (b) a coformer; and (ii) an amorphous form of Compound 1.

In one embodiment, provided herein is an unsolvated solid form comprising (a) Compound 1 and (b) a coformer. In one embodiment, provided herein is an anhydrous solid form comprising (a) Compound 1 and (b) a coformer. In one embodiment, provided herein is an unsolvated crystal form comprising (a) Compound 1 and (b) a coformer. In one embodiment, provided herein is an anhydrous crystal form comprising (a) Compound 1 and (b) a coformer. In one embodiment, provided herein is an unsolvated amorphous form comprising (a) Compound 1 and (b) a coformer. In one embodiment, provided herein is an anhydrous amorphous form comprising (a) Compound 1 and (b) a coformer. In one embodiment, the anhydrous form is substantially amorphous. In one embodiment, the anhydrous form is substantially crystalline. In one embodiment, provided herein is an unsolvated cocrystal comprising (a) Compound 1 and (b) a coformer. In one embodiment, provided herein is an anhydrous cocrystal comprising (a) Compound 1 and (b) a coformer.

In one embodiment, provided herein is a solvated solid form comprising (a) Compound 1 and (b) a coformer. In one embodiment, provided herein is a hydrated solid form comprising (a) Compound 1 and (b) a coformer. In one embodiment, provided herein is a solvated crystal form comprising (a) Compound 1 and (b) a coformer. In one embodiment, provided herein is a hydrated crystal form comprising (a) Compound 1 and (b) a coformer. In one embodiment, provided herein is a solvated amorphous form comprising (a) Compound 1 and (b) a coformer. In one embodiment, provided herein is hydrated amorphous form comprising (a) Compound 1 and (b) a coformer. In one embodiment, provided herein is a solvated cocrystal comprising (a) Compound 1 and (b) a coformer. In one embodiment, provided herein is a hydrated cocrystal comprising (a) Compound 1 and (b) a coformer. In certain embodiments, the solvated form is solvated by water, acetonitrile, diisopropyl ether, heptanes, ethyl acetate, methyl isobutyl ketone, or nitromethane. In certain embodiments, the hydrated form includes, but is not limited to, a hemihydrate, a monohydrate, a dihydrate, a trihydrate, and the like.

Solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., cocrystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In some embodiments, the cocrystal comprising (a) Compound 1 and (b) a coformer can be obtained by crystallization from certain solvent systems, for example, solvent systems comprising one or more of the following solvents: diisopropyl ether (IPE), isopropyl alcohol (IPA), methyl isobutyl ketone (MIBK), nitromethane, t-butyl methyl ether (MTBE), acetonitrile (MeCN), nitromethane, a mixture of 5% ethyl acetate and 95% heptanes. In a particular embodiment, the crystal form is solvated by diisopropyl ether. In certain embodiments, a solid form provided herein (e.g., a cocrystal comprising (a) Compound 1 and (b) a coformer) can be obtained by cooling and evaporation crystallization, slurry-ripening crystallization, temperature-cycling crystallization, and grinding crystallization.

(a) Methods of Preparing Cocrystals

Cocrystals provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid.

In certain embodiments, the coformer is a solid under ambient temperature conditions when in its pure form.

In certain embodiments, cocrystals can be prepared using solid-state methods such as solid-state grinding and solvent-drop grinding. In certain embodiments, cocrystals can be prepared using high-throughput screening. In certain embodiments cocrystals can be prepared using solution-based crystallization.

In certain embodiments, cocrystals formation can lead to enhancement of physical properties of the resulting solid forms, such as solubility, dissolution rate, bioavailability, physical stability, chemical stability, flowability, fractability, or compressibility.

In certain embodiments, provided herein are grinding methods for making a solid form cocrystal of Compound 1, comprising 1) adding Compound 1, conformers, and a solvent into a grinding machine equipped with one or two milling balls; 2) shaking the container for a particular time at a particular frequency at ambient temperature; and 3) collecting the resulting solid. In certain embodiments, the solvent is methyl t-butyl ether, methyl isobutyl ketone, and/or isopropyl alcohol. In one embodiment, the molar ratio of Compound 1 and the coformers is about 1:1. In certain embodiments, the period of time is about 15 minutes, about 20 minutes or about 30 minutes. In one embodiment, the frequency is about 15 Hz, about 20 Hz or about 30 Hz.

In certain embodiments, provided herein are slurry methods for making a solid form cocrystal of Compound 1, comprising 1) obtaining a slurry of Compound 1 and coformers in a ratio in a solvent; 2) stirring the slurry for a period of time while cycling the temperature between two set temperatures; 3) collecting a solid from the slurry by filtration (e.g., centrifuge filtration); and 4) drying the collected solids for a period of time to yield the solid form cocrystal of Compound 1. In certain embodiments, the solvent is acetonitrile, diisopropyl ether, a 95:5 mixture of heptane to ethyl acetate, methyl isobutyl ketone, or nitromethane. In one embodiment, the molar ratio of Compound 1 and the coformers is about 1:1. In one embodiment, the period of time is about 11 days. In one embodiment, the temperature was cycled between 40° C. and 5° C., for one hour at each temperature over the course of 11 days. In a particular embodiment, the coformer is isonicotinamide. In one embodiment, the solids are dried using air. In certain embodiments, the method further comprises the step of evaporating the supernatant under a flow of nitrogen gas at a certain temperature (e.g., ambient temperature) over a period of time to yield the solid form cocrystal of Compound 1.

In certain embodiments, provided herein are combinations of grinding and slurry methods comprising 1) adding Compound 1, a coformer, and a solvent into a grinding container equipped with one or two milling balls; 2) shaking the container for a particular time at a particular frequency; 3) collecting the solids and transferring them to vials containing a stir-disc with a solvent to obtain a slurry; 4) stirring the slurry for a period of time while cycling the temperature between two set temperatures; 5) collecting a solid from the slurry by filtration (e.g., centrifuge filtration); and 6) drying the collected solids for a period of time to yield the solid form cocrystal of Compound 1. In certain embodiments, the solvent employed in the grinding container is methyl t-butyl ether, methyl isobutyl ketone, and or isopropyl alcohol. In one embodiment, the molar ratio of Compound 1 and the coformers is about 1:1. In certain embodiments, the period of time of shaking the grinding container is 15 minutes, 20 minutes or about 30 minutes. In one embodiment, the frequency of shaking the grinding container is about 15 Hz, about 20 Hz or about 30 Hz. In one embodiment, the solvent used to obtain a slurry is acetonitrile, diisopropyl ether, methyl isobutyl ketone, or nitromethane. In one embodiment, the period of time for stirring the slurry is about 11 days. In one embodiment, the temperature of the slurry was cycled between 40° C. and 5° C., for one hour at each temperature over the course of 11 days. In one embodiment, the solids are dried using air. In certain embodiments, the method further comprises the step of evaporating the supernatant under a flow of nitrogen gas at a certain temperature (e.g., ambient temperature) over a period of time to yield the solid form cocrystal of Compound 1. In a particular embodiment, the coformer is resveratrol.

The solid form cocrystals provided herein may be characterized using a number of methods known to a person having ordinary skill in the art, including, but not limited to, single crystal X-ray diffraction, X-ray powder diffraction (PXRD), microscopy (e.g., scanning electron microscopy (SEM)), thermal analysis (e.g., differential scanning calorimetry (DSC), thermal gravimetric analysis (TGA), single differential thermal analysis (SDTA), and hot-stage microscopy), spectroscopy (e.g., infrared, Raman, and nuclear magnetic resonance), high performance liquid chromatography coupled with mass spectroscopy (HPLC-MS), thermogravimetrical analysis coupled with infrared analysis (TG-IR), and thermogravimetric analysis coupled with mass spectroscopy (TGA-MS). The particle size and size distribution of the solid form provided herein may be determined by conventional methods, such as laser light scattering technique.

The purity of the solid form cocrystals provided herein may be determined by standard analytical methods, such as thin layer chromatography (TLC), gel electrophoresis, gas chromatography, high performance liquid chromatography (HPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (2θ) (see, United States Pharmacopoeia, page 2228 (2003)).

(b) Cocrystal Form 1 Comprising Compound 1 and Resveratrol

Provided herein is cocrystal Form 1, comprising Compound 1 and resveratrol. In one embodiment, provided herein is a cocrystal comprising Compound 1 and resveratrol that is substantially crystalline. In one embodiment, provided herein is a solid form comprising a cocrystal comprising Compound 1 and resveratrol. In one embodiment, provided herein is a solid form comprising (i) a cocrystal comprising Compound 1 and resveratrol and (ii) an amorphous form of Compound 1. In one embodiment, provided herein is a solid form comprising (i) a cocrystal comprising Compound 1 and resveratrol and (ii) one or more additional crystal forms of Compound 1. Provided herein are various embodiments, preparations, or modifications of a cocrystal comprising Compound 1 and resveratrol.

In one embodiment, Form 1 is a diisopropyl ether solvated form comprising Compound 1 and resveratrol. In another embodiment, Form 1 is crystalline.

In certain embodiments, Form 1 is obtained by combinations of grinding and slurry experiments comprising 1) adding Compound 1, resveratrol and a solvent into a grinding container equipped with one or two milling balls; 2) shaking the container for a particular time at a particular frequency; 3) collecting the solids and transferring them to vials containing a stir-disc with a solvent to obtain a slurry; 4) stirring the slurry for a period of time while cycling the temperature between two set temperatures; 5) collecting a solid from the slurry by filtration; and 6) drying the collected solids for a period of time to yield the solid form cocrystal of Compound 1. In one embodiment, the solids are dried using air. In certain embodiments, the method further comprises the step of evaporating the supernatant under a flow of nitrogen gas at a certain temperature (e.g., ambient temperature) over a period of time to yield the solid form cocrystal of Compound 1. In certain embodiments, the solvent employed in the grinding container is methyl t-butyl ether, methyl isobutyl ketone or isopropyl alcohol. In one embodiment, the molar ratio of Compound 1 and the coformers is about 1:1. In certain embodiments, the period of time of shaking the grinding container is 20 minutes or about 30 minutes. In one embodiment, the frequency of shaking the grinding container is about 20 Hz or about 30 Hz. In one embodiment, the solvent used to obtain a slurry is acetonitrile, diisopropyl ether, methyl isobutyl ketone, or nitromethane. In one embodiment, the period of time for stirring the slurry is about 11 days. In one embodiment, the temperature of the slurry was cycled between 40° C. and 5° C., for one hour at each temperature over the course of 11 days.

Figure 1:
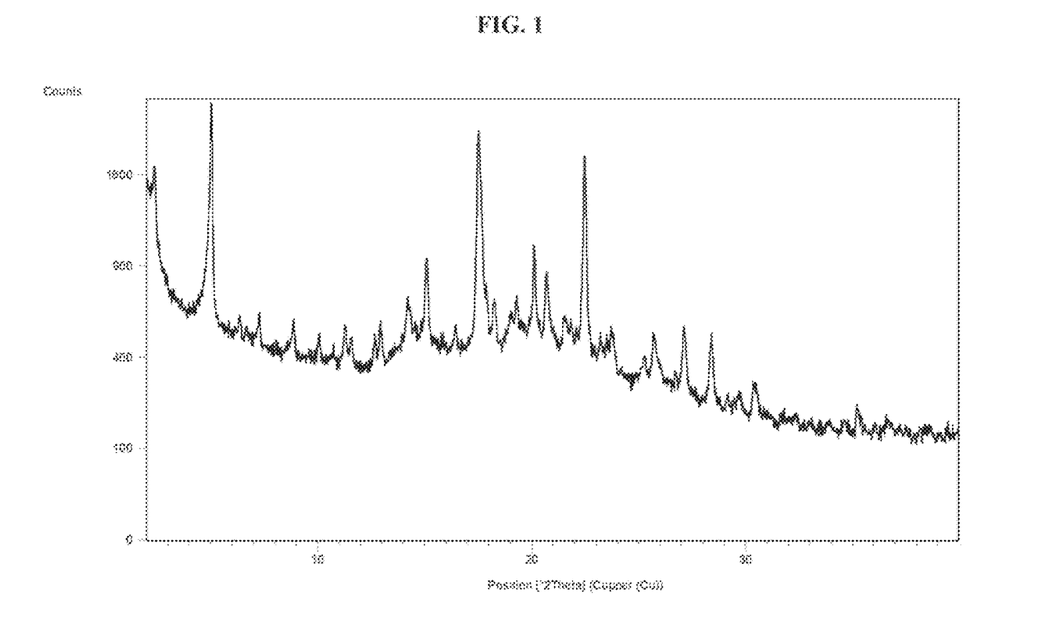
FIG. 1 depicts a PXRD pattern of Form 1.

In certain embodiments, a solid form provided herein, e.g., Form 1, is substantially crystalline, as indicated by, e.g., X-ray powder diffraction measurements. In one embodiment, Form 1 of Compound 1 has an X-ray powder diffraction pattern substantially as shown in FIG. 1. In one embodiment, Form 1 of Compound 1 has an X-ray powder diffraction pattern comprising one or more characteristic X-ray powder diffraction peaks at a two-theta angle of approximately 2.4, 5.1, 8.9, 11.3, 12.9, 14.2, 15.1, 17.5, 18.3, 19.3, 20.1, 20.7, 22.5, 25.7, 27.1, and 28.4 degrees as depicted in FIG. 1. In one embodiment, Form 1 of Compound 1 has an X-ray powder diffraction pattern comprising one or more characteristic X-ray powder diffraction peaks at a two-theta angle of approximately 2.4, 5.1, 14.2, 15.1, 17.5, 18.3, 19.3, 20.1, 20.7, 22.5, 27.1, and 28.4 degrees as depicted in FIG. 1. In one embodiments, Form 1 of Compound 1 has an X-ray powder diffraction pattern comprising of one or more characteristic X-ray powder diffraction peaks at a two-theta angle of approximately 2.4, 5.1, 15.1, 17.5, 20.1, and 22.5 degrees as depicted in FIG. 1.

Figure 2:
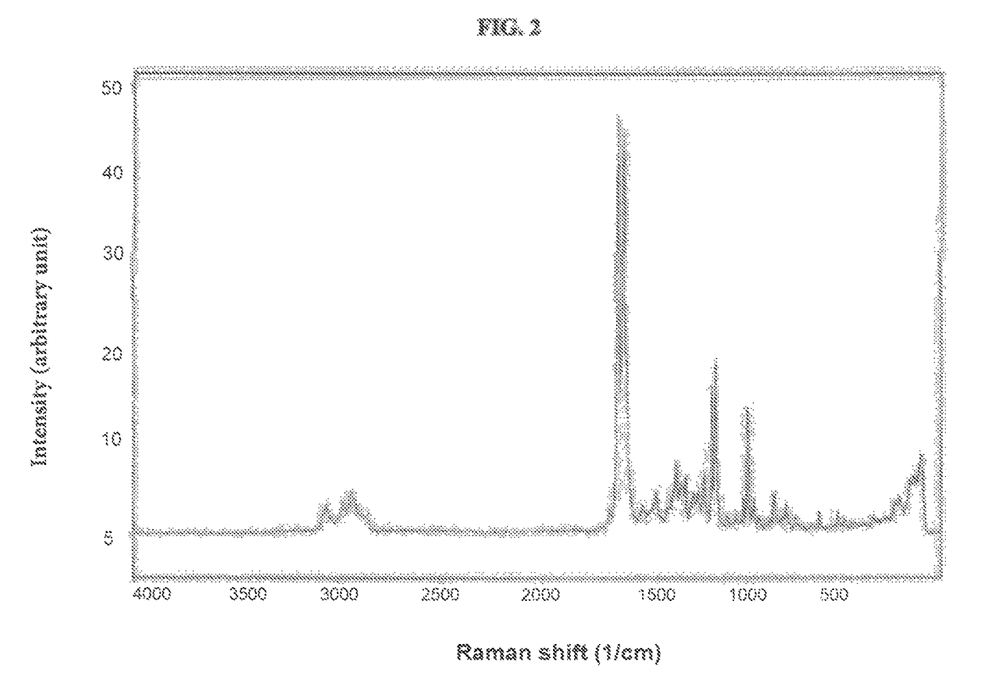
FIG. 2 depicts an FT-Raman spectrum of Form 1.

In one embodiment, provided herein is Form 1 having an FT-Raman Spectrum as depicted in FIG. 2.

Figure 3:
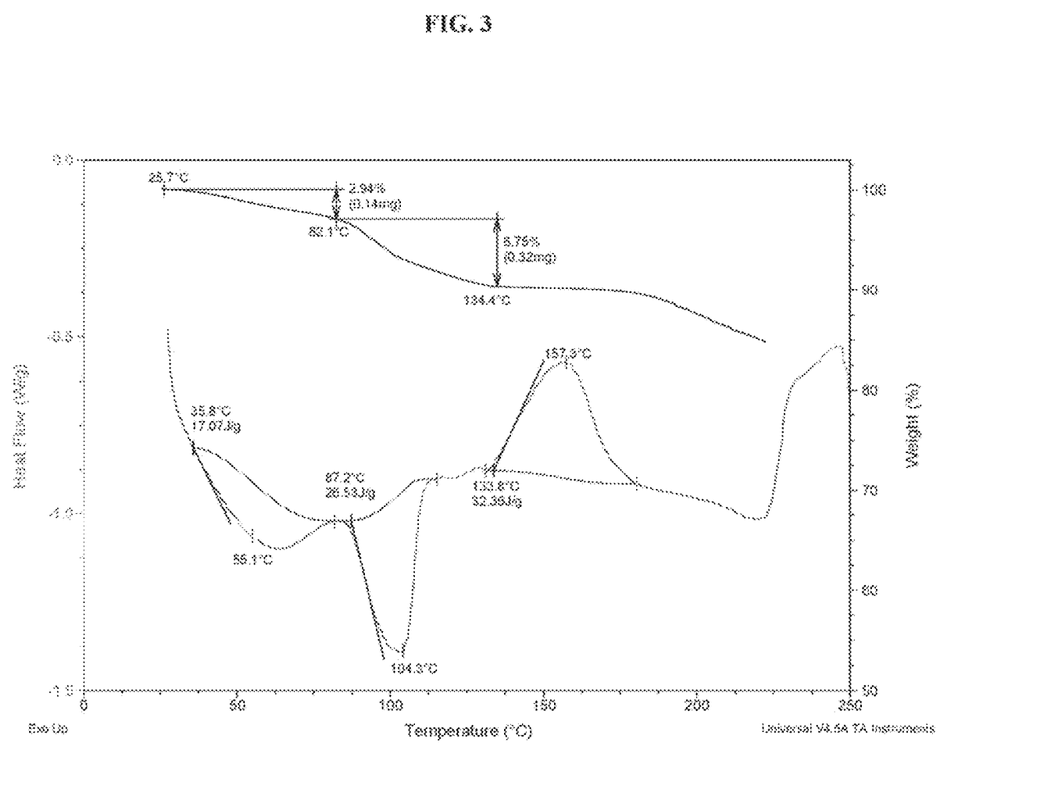
FIG. 3 depicts differential scanning calorimetry/thermal gravimetric analysis of Form 1.
Figure 4:
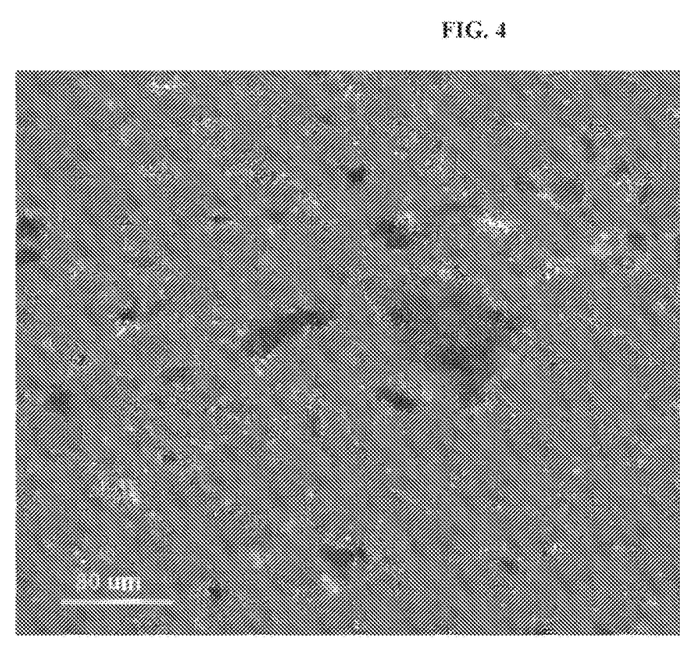
FIG. 4 depicts polarized-light microscopy of Form 1.

In one embodiment, provided herein is a solid form, e.g., Form 1 of Compound 1, having a DSC thermograph substantially as depicted in FIG. 3. In one embodiment, DSC analysis of Form 1 of Compound 1 showed a possible dehydration endotherm with onset at 35.8° C., a possible desolvation endotherm with onset at 87.2° C., and a possible decomposition exotherm with onset at 134° C.

In on embodiment, provided herein is a solid form, e.g., Form 1 of Compound 1, having a TGA thermograph corresponding substantially to the representative TGA thermograph as depicted in FIG. 3. In one embodiment, TGA-IR analysis of Form 1 of Compound 1 showed a low-temperature (26-82° C.) loss of about 2.9% water, followed by a loss of about 6.8% of diisopropyl ether from 82° C. to 134° C. on heating. In one embodiment, Proton NMR analysis of Form 1 of Compound 1 indicated a 1:1 stoichiometry of Compound 1 to resveratrol.

In still another embodiment, Form 1 of Compound 1 is substantially pure. In certain embodiments, the substantially pure Form 1 of Compound 1 is substantially free of other solid forms, e.g., amorphous form. In certain embodiments, the purity of the substantially pure Form 1 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.4 Methods of Use

The solid forms and the pharmaceutical compositions provided herein can be used in all the methods provided herein. The solid forms and the pharmaceutical compositions provided herein can be used in the treatment of all diseases, disorders or conditions provided herein.

Provided herein are methods for treating a subject suffering from or at risk for having an autoimmune disease or chronic inflammatory disorder, wherein the method comprises administering to said subject a solid form of Compound 1 provided herein or a pharmaceutical composition thereof. In certain embodiments, the autoimmune or chronic inflammatory disorder is polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis. In a preferred embodiment, the multiple sclerosis is relapsing-remitting multiple sclerosis, primary progressive multiple sclerosis, secondary progressive multiple sclerosis, or relapsing secondary progressive multiple sclerosis.

In certain embodiments, the solid form is cocrystal Form 1. In certain embodiments, Form 1 comprises Compound 1 and resveratrol.

In another embodiment, provided herein are methods for treating a subject suffering from or at risk for having a neurological disorder, wherein the method comprises administering to said subject a solid form of Compound 1 provided herein or a pharmaceutical composition thereof. In one embodiment, the neurological disorder is Rett Syndrome. In certain embodiments, the solid form is Form 1. In certain embodiments, Form 1 comprises Compound 1 and resveratrol.

In another embodiment, provided herein are methods for treating a subject suffering from or at risk for renal or hepatic impairment, wherein the method comprises administering to said subject a solid form of Compound 1 provided herein or a pharmaceutical composition thereof. In certain embodiments, the solid form is Form 1. In certain embodiments, Form 1 comprises Compound 1 and resveratrol.

In another embodiment, provided herein are methods for treating a subject suffering from or at risk for a disease or disorder mediated by lymphocyte interactions, wherein the method comprises administering to said subject a solid form of Compound 1 provided herein or a pharmaceutical composition thereof. In certain embodiments, the disease or disorder mediated by lymphocyte interactions is, for example, in transplantation, acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus. In certain embodiments, the solid form is Form 1. In certain embodiments, Form 1 comprises Compound 1 and resveratrol.

In another embodiment, provided herein are methods for the treatment of a disease or disorder associated with sphingosine 1-phosphate, wherein the method comprises administering to said subject a solid form of Compound 1 provided herein or a pharmaceutical composition thereof. In certain embodiments, the disease or disorder associated with sphingosine 1-phosphate is multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease. In certain embodiments, the solid form is Form 1. In certain embodiments, Form 1 comprises Compound 1 and resveratrol.

In another embodiment, provided herein are methods for the treatment of a disease or disorder associated with the interferon alpha receptor 1, wherein the method comprises administering to said subject a solid form of Compound 1 or a pharmaceutical composition thereof. In certain embodiments, the disease or disorder associated with the interferon alpha receptor is psoriasis, ulcerative colitis, systemic lupus, multiple sclerosis, or rheumatoid arthritis. In one embodiment, the solid form is Form 1. In certain embodiments, Form 1 comprises Compound 1 and resveratrol.

The compounds, compositions, methods, and uses disclosed herein are not to be limited in scope by the specific embodiments described herein. Indeed, various modifications of the compounds, compositions, methods, and uses in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entities.

5.5 Pharmaceutical Compositions

Solid forms of Compound 1 provided herein are useful for the preparation of pharmaceutical compositions, comprising an effective amount of a solid form of Compound 1 and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration. In one embodiment, the solid form is Form 1. In certain embodiments, Form 1 comprises Compound 1 and resveratrol.

5.6 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches, calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL 200 (W.R. Grace Co., Baltimore, Md.) and CAB-O-SIL (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

5.7 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

6. EXAMPLES

The following Examples are presented by way of illustration, not limitation.

6.1 Analytical Methods

PXRD patterns were obtained using a PANalytical X'Pert Pro diffractometer using Ni-filtered Cu Ka (45 kV/40 mA) radiation and a step size of 0.02° 2θ and X'celerator Real Time Multi-Strip (RTMS) detector. Configuration on the incidental beam side is a fixed divergence slit (0.25°), 0.04 radian Soller slits, anti-scatter slit (0.25°), and 10 mm beam mask. Configuration on the diffracted beam side is a fixed divergence slit (0.25°) and 0.04 radian Soller slit. Samples were mounted flat on zero-background Si wafers and covered with Kapton film to comply with safety policies.

FT-Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. Spectra were acquired at 4 cm$^{-1}$ resolution, 64 scans, using Happ-Genzel apodization function and 2-level zero-filling.

Differential Scanning Calorimetry (DSC) was conducted with a TA Instruments Q100 differential scanning calorimeter equipped with an autosampler and a refrigerated cooling system under 40 mL/min N$_2$ purge. DSC thermograms were obtained at 15° C./min in crimped Al pans.

Polarized-light microscopy (PLM) photomicrographs were collected using an Olympus BX60 polarized-light microscope equipped with an Olympus DP70 camera.

Thermogravimetric Analysis (TGA) thermograms were obtained with a TA Instruments Q500 thermogravimetric analyzer under 40 mL/min N2 purge at 15° C./min in Al pans.

Thermogravimetric Analysis with IR Off-Gas Detection (TGA-IR) was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N$_2$ flow and heating rate of 15° C./min in Al pans. IR spectra were collected at 4 cm$^{-1}$ resolution and 32 scans at each time point.

Proton Nuclear Magnetic Resonance ($^1$H NMR) spectra were collected using an Agilent DD2 500 MHz spectrometer with tetramethylsilane reference. Samples were dissolved in deuterated dimethyl sulfoxide.

6.2 Form 1: Siponimod/Resveratrol Cocrystal

Compound 1 (100 mg) was combined with resveratrol (42.5 mg) and about 2 μL of methyl isobutyl ketone in a stainless steel milling jar. Grinding was conducted on a Retsch Mill (Model M301) at room temperature with two milling balls (7 mm) at 20 Hz for 20 minutes or at 15 Hz for 15 minutes. The ground solids (40.7 mg) were transferred into 2 mL vials containing a stir-disc and combined with 500 μL of diisopropyl ether. The sample was stirred for 11 days while cycling the temperature between 40° C. and 5° C. (1 h at each temperature). Suspended solids were isolated by filtration and air-dried for 1-2 hours to yield Form 1 of Compound 1.

Form 1 has an FT-Raman Spectrum as depicted in FIG. 2. Form 1 has a DSC thermograph substantially as depicted in FIG. 3, comprising an endothermic event with an onset temperature of about 35.8° C. In addition, DSC analysis showed a possible desolvation endotherm with onset at about 87.2° C., and a possible decomposition endotherm with onset at about 134° C. Form 1 has a TGA thermograph as depicted in FIG. 3, comprising a mass loss of approximately 3.0% between 26° C. and 82° C., and a mass loss of about 6.8% of the sample when heated from approximately 82° C. and 134° C.

A list of X-Ray Diffraction Peaks for Form 1 is provided below in Table 1.

TABLE 1

X-Ray Diffraction Peaks for Form 1.

| Two-theta angle (°) | d Space (Å) | Height (counts) |
|---|---|---|
| 2.4 | 37.011 | 546.4 |
| 5.1 | 17.468 | 1673.2 |
| 6.3 | 13.961 | 71.5 |
| 7.3 | 12.154 | 144.6 |
| 8.9 | 9.959 | 153.7 |
| 10.1 | 8.792 | 113.4 |
| 11.3 | 7.836 | 172.4 |
| 11.6 | 7.646 | 131.5 |
| 12.7 | 6.995 | 108.4 |
| 12.9 | 6.841 | 173.1 |
| 14.2 | 6.234 | 268.4 |
| 15.1 | 5.855 | 510.7 |
| 16.5 | 5.387 | 100.1 |
| 17.5 | 5.065 | 1567.8 |
| 18.3 | 4.854 | 238.9 |
| 19.3 | 4.602 | 234.8 |
| 20.1 | 4.411 | 572.9 |
| 20.7 | 4.293 | 356.6 |
| 21.5 | 4.129 | 131.9 |
| 22.5 | 3.956 | 1364.4 |
| 23.7 | 3.747 | 149.8 |
| 25.7 | 3.463 | 192.1 |
| 27.1 | 3.287 | 280.8 |
| 28.4 | 3.143 | 262.9 |
| 29.7 | 3.005 | 58.6 |
| 30.4 | 2.943 | 108.9 |
| 35.2 | 2.548 | 77.9 |

6.3 Evaluation of Solid Forms (a) Solubility Measurements

A weighed sample of Form 1 is treated with aliquots of the test solvent at ambient temperature or elevated temperature. Complete dissolution of the test material is determined by visual inspection. Solubility was estimated based on the total solvent used to provide complete dissolution of the sample. The actual solubility may be greater than the value calculated because of the use of solvent aliquots that were too large or due to a slow rate of dissolution.

(b) Stability Measurements

The stability of Form 1 is determined by exposing the sample to a 40° C./75% relative humidity (RH) environment for four weeks or 11% RH at ambient temperature for four days.

(c) S1P1 Assays

The compounds are useful in the treatment of a variety of S1P1 receptor-mediated clinical conditions, including autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the solid forms of the invention may be assayed for their ability to modulate the S1P1 receptor activity. See Colandrea, Biorg. Med. Chem. Lett. 2006, 16(11):2905-2908.

(i) In Vitro Binding Assay

The solid forms described herein (e.g., Form 1) are evaluated using a [$^{35}$S]-GTP-gamma-S binding assay to monitor dose-dependent selectivity against S1P1 receptors. The assay is completed with sample solid forms subjected to an eight-point, four-fold dose response curve with starting concentration of 10 M. Selectivity is determined upon initial addition of solid forms followed by an incubation period. Following compound incubation, bounded [35S]-GTP-gamma-S is determined by filtration and scintillation counting. Percentage activation and inhibition values are determined relative to the reference agonist at S1P.

(ii) In Vivo Blood Lymphocyte Depletion Assay

In addition to their S1P1 binding properties, modulators of the S1P receptor also have accelerating lymphocyte homing properties. These properties may be measured using a blood lymphocyte depletion assay. The solid forms described herein (e.g., Form 1) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

(d) In Vitro Metabolic Disposition in Liver Microsomal Fractions

The stability of the solid forms described herein (e.g., Form 1) is determined according to standard procedures known in the art. For example, stability of Form 1 is established by an in vitro assay. An in vitro hepatic microsome stability assay measures the stability of one or more subject compounds when reacting with mouse, rat or human microsomes.

Incubations with liver microsomes are conducted in a final volume of 0.1 mL per incubation time point. 10 µM of the subject solid form from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM MgCl2, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form comprising greater than 80% by weight of a cocrystal comprising (a) compound 1, or a tautomer thereof and (b) a coformer.

2. The solid form of claim 1, wherein the coformer is resveratrol, caffeine, theophyline, isonicotinamide, xylitol, adenine, 2-aminopyridine, saccharin, vanillyl alcohol, chrysin, glutamine, acetamide, urea, or nicotinamide.

3. The solid form of claim 1, which is substantially crystalline.

4. The solid form of claim 2, wherein the coformer is isonicotinamide.

5. The solid form of claim 1, which is greater than 90% by weight of a cocrystal.

6. The solid form of claim 1, which is substantially physically pure.

7. The solid form of claim 1, which is diisopropyl ether solvated.

8. The solid form of claim 1, which is substantially free of other solid forms of compound 1.

9. The solid form of claim 1, further comprising amorphous compound 1.

10. The solid form of claim 9, which is substantially crystalline.

11. A pharmaceutical composition comprising the solid form of claim 1.

12. The pharmaceutical composition of claim 11, further comprising a pharmaceutically acceptable excipient or carrier.

13. The pharmaceutical composition of claim 12, wherein the pharmaceutical composition is a single unit dosage form.

14. The pharmaceutical composition of claim 13, wherein the single unit dosage form comprises about 0.5 mg, about 2 mg, or about 10 mg of compound 1.

15. The pharmaceutical composition of claim 11, wherein the pharmaceutical composition is a tablet.

16. The pharmaceutical composition of claim 11, wherein the pharmaceutical composition is a capsule.

17. The solid form of claim 1, comprising greater than 95% by weight of a cocrystal comprising (a) compound 1 or a tautomer thereof and (b) a coformer.

18. The solid form of claim 1, comprising greater than 97% by weight of a cocrystal comprising (a) compound 1 or a tautomer thereof and (b) a coformer.

19. The solid form of claim 1, comprising greater than 99% by weight of a cocrystal comprising (a) compound 1 or a tautomer thereof and (b) a coformer.

20. A solid form comprising greater than 80% by weight of a cocrystal comprising
(a) compound 1 or a tautomer thereof and (b) resveratrol.

21. The solid form according to claim 20, comprising greater than 90% by weight of a cocrystal comprising (a) compound 1 or a tautomer thereof; and (b) resveratrol.

22. The solid form according to claim 20, comprising greater than 95% by weight of a cocrystal comprising (a) compound 1 or a tautomer thereof; and (b) resveratrol.

23. The solid form according to claim 20, comprising greater than 97% by weight of a cocrystal comprising (a) compound 1 or a tautomer thereof; and (b) resveratrol.

24. The solid form according to claim 20, comprising greater than 99% by weight of a cocrystal comprising (a) compound 1 or a tautomer thereof; and (b) resveratrol.

\* \* \* \* \*